United States Patent [19]

Rizkalla

[11] 4,328,362

[45] May 4, 1982

[54] CONVERSION OF ACETIC ANHYDRIDE TO ETHYLIDENE DIACETATE

[75] Inventor: Nabil Rizkalla, River Vale, N.J.

[73] Assignee: The Halcon SD Group, Inc., New York, N.Y.

[21] Appl. No.: 219,785

[22] Filed: Dec. 24, 1980

[51] Int. Cl.³ .................. C07C 67/00; C07C 69/16
[52] U.S. Cl. .................................. 560/263; 560/265; 562/607; 568/484
[58] Field of Search ......................................... 560/263

[56] References Cited

FOREIGN PATENT DOCUMENTS 1538782  1/1979  United Kingdom ................ 560/263

*Primary Examiner*—Vivian Garner
*Attorney, Agent, or Firm*—William C. Long; David Dick; Riggs T. Stewart

[57] ABSTRACT

Acetic anhydride is reacted with hydrogen to produce ethylidene diacetate by carrying out the reaction in the presence of a catalyst comprising a molybdenum-nickel or a tungsten-nickel co-catalyst component and in the presence of an iodide and a promoter comprising an organo-phosphorus compound or an organo-nitrogen compound wherein the phosphorus and the nitrogen are trivalent.

4 Claims, No Drawings

CONVERSION OF ACETIC ANHYDRIDE TO ETHYLIDENE DIACETATE

This invention relates to the preparation of ethylidene diacetate and is more particularly concerned with the preparation of this ester by the action of hydrogen on acetic anhydride.

Ethylidene diacetate is a chemical intermediate of prime commercial interest in view of its ready convertibility to a number of different tonnage chemicals of commerce. By one known conversion technique, ethylidene diacetate is readily transformed to vinyl acetate plus acetic acid; see Kirk-Othmer "*Encyclopedia of Chemical Technology,*" (2nd ed.), vol. 21, page 321, Interscience, New York (1970). By another well-known conversion process, ethylidene diacetate can be transformed into acetic anhydride plus acetaldehyde; see Kirk-Othmer "*Encyclopedia of Chemical Technology,*" (2nd ed.), vol. 8, pages 410–413, Interscience, New York (1965). Reference is also made to U.S. Pat. No. 2,425,389 as indicative of the flexibility of ethylidene diacetate as a chemical intermediate.

Various processes have been proposed for the preparation of ethylidene diacetate. One such process involves the reaction of acetaldehyde and acetic anhydride, the ethylidene diacetate being produced as an intermediate in the preparation of vinyl acetate, a process which has been employed to a limited extent on a commercial scale; see "Hydrocarbon Process" 44 (11), 287 (1965). British Pat. No. 1,538,782 discloses another technique for producing ethylidene diacetate which employs the carbonylation of methyl acetate or dimethyl ether in the presence of hydrogen. Fenton U.S. Pat. No. 3,579,566 treats organic acid anhydrides such as acetic anhydride with hydrogen in the presence of a catalyst comprising a complex of a Group VIII noble metal with a biphyllic ligand from the group consisting of trihydrocarbyl phosphines, arsines and stibines. The Fenton examples show the preparation of ethylidene diacetate from acetic anhydride by this technique.

The Fenton examples, however, show that the quantity of ethylidene diacetate which is produced is relatively small in relation to the theoretical quantity producible from the acetic anhydride employed. While Fenton illustrates his generic process in terms of the following "shorthand" equation:

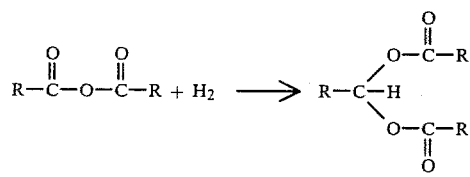

the complete equation is as follows:

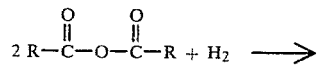

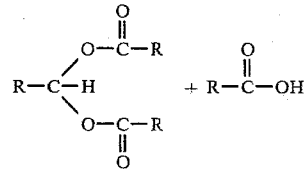

In the foregoing equation, when R is —CH$_3$ the treatment of acetic anhydride with hydrogen is illustrated. In other words, in such a reaction, one molecule of acetic acid is formed for each molecule of ethylidene diacetate produced. Competing reactions tend to form other products such as acetaldehyde and ethyl acetate, to the detriment of the yield of ethylidene diacetate.

Moreover, the Group VIII noble metals, i.e., ruthenium, rhodium, palladium, osmium, iridium and platinum are relatively expensive metals but their use has heretofore been considered essential in the conversion of acetic anhydride to ethylidene diacetate.

It is accordingly an object of the invention to provide an improved process for the preparation of ethylidene diacetate from acetic anhydride which does not require the use of Group VIII noble metals.

In accordance with the invention, this and other objects are realized by the reaction of acetic anhydride with hydrogen in using a molybdenum-nickel or a tungsten-nickel co-catalyst in the presence of a promoter comprising an organo-phosphorus compound or an organo-nitrogen compound wherein the phosphorus and nitrogen are trivalent, and in the presence of an iodide. The surprising discovery has been made that this co-catalyst in combination with the promoter-iodide system of the character indicated makes possible conversion of acetic anhydride to ethylidene diacetate not only at relatively low pressures and without the use of expensive Group VIII noble metals but also leads to attractive yields of ethylidene diacetate.

Thus, in accordance with the invention, hydrogen is reacted with acetic anhydride in the presence of an iodide, e.g., a hydrocarbyl iodide, especially a lower alkyl iodide, such as methyl iodide. Thus, ethylidene diacetate can be effectively prepared in a representative case by subjecting acetic anhydride to reaction with hydrogen in the presence of methyl iodide and in the presence of the co-catalyst promoter-system described above. In all cases, the reaction is carried out under anhydrous conditions.

In carrying out the process of the invention, a wide range of temperatures, e.g., 50° to 250° C. are suitable but temperatures of 100° to 200° C. are preferably employed and the more preferred temperatures generally lie in the range of 100° to 160° C. Temperatures lower than those mentioned can be used but they tend to lead to reduced reaction rates, and higher temperatures may also be employed but there is no particular advantage in their use. Preferably the reaction is carried out at a substantially constant temperature.

The time of reaction is also not a parameter of the process and depends largely upon the temperature employed, but typical reaction or residence times, by way of example, will generally fall in the range of 0.1 to 4 hours. The reaction is carried out under super-atmospheric pressures but excessively high pressures, which require special high-pressure equipment, are not necessary. In general, the reaction is effectively carried out by employing a hydrogen partial pressure which is preferably 50 to 2,000 p.s.i., and most preferably 300 to 700 p.s.i., although hydrogen partial pressures of 1 to 10,000 p.s.i. can also be employed. In the usual case, pressures below about 2,000 psi are generally used. By maintaining the partial pressure of hydrogen at the values specified, adequate amounts of this reactant are always present. The total pressure is preferably that required to maintain the liquid phase and, in this case, the reaction can be advantageously carried out in an autoclave or similar apparatus.

At the end of the desired residence time, the reaction mixture is separated into its several constituents, as by distillation. Preferably, the reaction product is introduced into a distillation zone, which may be a fractional distillation column, or a series of columns, effective to separate the unreacted acetic anhydride, acetic acid, other by-products, if present, and other volatile components such as methyl iodide, from the product ethylidene diacetate. The boiling points of these several compounds are sufficiently far apart that their separation by conventional distillation presents no particular problem. Likewise, the higher boiling ethylidene diacetate can be readily distilled away from the relatively non-volatile catalyst components.

The hydrogen is preferably employed in substantially pure form, as available commercially, but inert diluents such as carbon monoxide, carbon dioxide, nitrogen, methane, and noble gases can be present if desired. The presence of inert diluents does not affect the reaction but their presence makes it necessary to increase the total pressure in order to maintain the desired hydrogen partial pressure. The hydrogen, like other reactants should, however, by essentially dry, i.e., the hydrogen and the other reactants should be reasonably free from water. The presence of minor amounts of water such as may be found in the commercial forms of the reactants is, however, entirely acceptable. It is preferable that the amount of moisture be kept to a minimum, since the presence of water has been found to have an adverse effect upon the activity of the co-catalyst promoter system.

The co-catalyst components can be employed in any convenient form, viz, in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus typical compounds include the carbonate, oxide, hydroxide, bromide, iodide, chloride, oxyhalide, hydride, lower alkoxide (methoxide), phenoxide, or molybdenum, tungsten or nickel carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the co-catalyst components with organic promoter ligands derived from the organic promoters hereinafter described.

Particularly preferred are the elemental forms, compounds which are iodides, and organic salts, e.g., salts of the monocarboxylic acid corresponding to the anhydride being used. It will be understood that the foregoing compounds and complexes are merely illustrative of suitable forms of the nickel and co-catalyst components and are not intended to be limiting.

The nickel and co-catalyst components employed may contain impurities normally associated with the commercially available metal or metal compounds and need not be purified any further.

The promoter is, as said, an organo-phosphorus or nitrogen compound, wherein P and N are trivalent. The organo-phosphorus promoter is preferably a phosphine, e.g., a phosphine of the formula

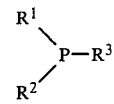

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine.

Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexyl-methylamine, 2-6-diaminopyridine, 2-quinolinol, N,N-diethyltoluamide, and imidazole.

Although generally the organic promoters are added separately to the catalyst system, it is also possible to add them as complexes with the co-catalyst metals such as bis(triphenylphosphine) nickel dicarbonyl and tetrakis (triphenyl phosphite) nickel. Both free organic promoters and complexed promoters can also be used. Indeed, when a complex of the organic promoter and the co-catalyst metals is used, free organic promoter can also be added as well.

The amount of each co-catalyst component is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 mol per 10 to 10,000 mols of acetic anhydride, preferably 1 mol per 100 to 5,000 mols of acetic anhydride and most preferably 1 mol per 500 to 1,000 mols of acetic anhydride.

The ratio of nickel to the other co-catalyst component can vary. Typically, it is one mol of the nickel component per 0.01 to 100 mols of the other co-catalyst component, preferably the nickel component is used in the amount of 1 mol per 0.1 to 20 mols, most preferably 1 mol per 1 to 10 mols of the other co-catalyst component.

The quantity of organic promoter can also vary widely but typically it is used in the amount of 1 mol per 0.1 to 10 mols of co-catalyst components, preferably 1 mol per 0.5 to 5 mols, most preferably 1 mol per 1 to 5 mols of co-catalyst components.

The amount of iodide component may also vary widely but, in general, it should be present in an amount of at least 10 mols (expressed as I) per hundred mols of acetic anhydride. Typically, there are used 10 to 50 mols of the iodide per 100 mols of acetic anhydride, preferably 17 to 35 mols per 100 mols. Ordinarily, more than 200 mols of iodide per 100 mols of acetic anhydride are not used. It will be understood, however, that the iodide moiety does not have to be added to the system as a hydrocarbyl iodide but may be supplied as another organic iodide or as the hydroiodide or other inorganic iodide, e.g., a salt, such as the alkali metal or other metal salt, or even as elemental iodide.

The process of this invention can be carried out in the presence of a solvent or diluent, if desired. Ordinarily, a solvent is not required. The solvent or diluent can be any organic solvent which is inert in the environment of the process, such as hydrocarbons, e.g., octane, benzene, toluene, xylene and Tetralin, or halogenated hydrocarbons such as the chlorobenzenes, e.g., trichlorobenzene, or carboxylic acids, e.g., acetic acid, or esters such as methyl acetate and Cellosolve acetate, and the like. Preferred solvents are acetic acid and trichlorobenzene. In general, acetic acid has been found to be the most suitable for use when a solvent is employed in the process. A solvent or diluent is suitably selected which has a boiling point sufficiently different from the other components in the reaction mixture that it can be readily separated by distillation, as will be readily apparent to persons skilled in the art.

A particular embodiment of the catalyst comprising the molybdenum-nickel or tungsten-nickel co-catalyst component, the organic promoter component and the iodide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is an iodide source which is hydrogen iodide, iodine, an alkyl iodide wherein the alkyl group contains 1 to 20 carbon atoms or an alkali metal iodide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of ethylidene diacetate, with the other organic components being recycled and, in the case of liquid-phase reaction, a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported. i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention.

EXAMPLE 1

A pressure vessel made of Hastelloy-C is charged with a mixture containing 30.25 weight percent acetic anhydride, 56 weight percent methyl iodide, 1.25 weight percent bis-triphenylphosphine nickel dicarbonyl, 5 weight percent triphenylphosphine, 2.5 weight percent molybdenum hexacarbonyl, and 5 weight percent acetic acid. The vessel is swept out with argon and pressured to 300 psig with carbon monoxide and to 600 psig with hydrogen. Then the vessel is heated to 145° C. with stirring and at this temperature the pressure is 940 psig. The vessel is further pressured up to 1,200 psig using hydrogen and is maintained at this pressure by recharging hydrogen when needed, the temperature being maintained at 145° C. After 8 hours reaction time, Gas Chromotographic (G. C.) analysis of the reaction mixture shows it to contain 13.1 weight percent ethylidene diacetate.

EXAMPLE 2

A pressure vessel as described in Example 1 is charged with a mixture containing 46 weight percent acetic anhydride, 46 weight percent methyl iodide, 1 weight percent bis-triphenylphosphine nickel dicarbonyl, 4 weight percent triphenylphosphine, and 2 weight percent molybdenum hexacarbonyl. The vessel is swept out with argon and pressured to 200 psig with carbon monoxide and to 400 psig with hydrogen. Then the vessel is heated to 155° C. with stirring and at this temperature the pressure is 760 psig. The vessel is pressured to 1,200 psig using hydrogen and is maintained at this pressure by recharging hydrogen when needed, the temperature being maintained at 155° C. After 2¼ hours reaction time, G. C. analysis of the reaction mixture shows it to contain 9.6 weight percent ethylidene diacetate.

EXAMPLE 3

Again using a pressure vessel as described in Example 1, the reactor is charged with a mixture containing 46 weight percent acetic anhydride, 46 weight percent methyl iodide, 1 weight percent bis-triphenylphosphine nickel dicarbonyl, 4 weight percent triphenylphosphine, and 2 weight percent molybdenum hexacarbonyl. The vessel is swept out with argon and pressured to 400 psig with hydrogen and is heated to 155° C. with stirring. At this temperature the pressure is 610 psig. The vessel is then pressured to 1200 psig with hydrogen and is maintained at this pressure by recharging hydrogen when needed, the temperature being maintained at 155° C. After 2 hours reaction time, G. C. analysis of the reaction mixture shows it to contain 12 weight percent ethylidene diacetate.

EXAMPLE 4

Example 1 is repeated with the exception that molybdenum hexacarbonyl is replaced with tungsten hexacarbonyl. After a reaction time of 8 hours, the reaction mixture corresponds to that obtained in Example 1.

EXAMPLE 5

Example 1 is repeated with the exception that molybdenum hexacarbonyl is replaced with chromium hexacarbonyl. After a reaction time of 8 hours, G. C. analysis of the reaction mixture shows it to contain only traces of ethylidene diacetate.

EXAMPLE 6

When Example 1 is repeated using an equivalent amount of nickel hexacarbonyl as the Ni component and an equivalent amount of imidazole instead of triphenylphosphine, the reaction mixture is found to contain 8 weight percent ethylidene diacetate.

What is claimed is:

1. A process for the conversion of acetic anhydride which comprises reacting said acetic anhydride under anhydrous conditions with hydrogen in the presence of a molybdenum-nickel co-catalyst or a tungsten-nickel co-catalyst, in the presence of an iodide and in the presence as a promoter of an organo-phosphorus compound or an organo-nitrogen compound wherein the phosphorus and the nitrogen are trivalent.

2. A process as defined in claim 1, wherein the co-catalyst is molybdenum-nickel.

3. A process as defined in claim 1, wherein the promoter is a phosphine.

4. A process as defined in claim 1, wherein the co-catalyst is molybdenum-nickel and the promoter is a phosphine.

* * * * *